(12) United States Patent
Zhang

(10) Patent No.: US 8,715,737 B2
(45) Date of Patent: May 6, 2014

(54) METHOD TO MAKE POROUS MATERIALS AND THEIR APPLICATIONS

(76) Inventor: Zhuo Joe Zhang, Clarksburg, MD (US)

( * ) Notice: Subject to any disclaimer, the term of this patent is extended or adjusted under 35 U.S.C. 154(b) by 936 days.

(21) Appl. No.: 12/691,194

(22) Filed: Jan. 21, 2010

(65) Prior Publication Data

US 2011/0176997 A1    Jul. 21, 2011

(51) Int. Cl.
*A61K 9/14* (2006.01)
*A61K 51/00* (2006.01)

(52) U.S. Cl.
USPC ......... 424/489; 424/1.69; 424/1.73; 514/776; 514/777; 514/183; 514/561

(58) Field of Classification Search
None
See application file for complete search history.

(56) References Cited

U.S. PATENT DOCUMENTS

2008/0145658 A1* 6/2008 Richard et al. ............... 428/402
2010/0111860 A1* 5/2010 Luo et al. ..................... 424/1.73

OTHER PUBLICATIONS

Saha, T.K., et al., "Gadolinium diethylenetriaminopentaacetic acid-loaded chitosan microspheres for gadolinium neutron-capture therapy", 2006, Carbohydrate Research, 341, pp. 2835-2841.*
Hu, Z.G., et al., "The sorption of acid dye onto chitosan nanoparticles", 2006, Polymer, 47, pp. 5838-5842.*
Atala, A., et al., "Method of Tissue Engineering", Elsevier, 2002, p. 566.*
Orrego, C.E., et al., "Preparation and characterization of chitosan membranes by using a combined freeze gelation and mild crosslinking method", 2009, Bioprocess Biosyst Eng., 32, pp. 197-206.*
Chung, T.W., et al., "Preparation of alginate/galactosylated chitosan scaffold for hepatocyte attachment", 2002, Biomaterials, pp. 2827-2834.*
Petition for Extension of Time U.S. Appl. No. 12/691,194; May 24, 2010.

* cited by examiner

*Primary Examiner* — Michael G Hartley
*Assistant Examiner* — Lance Rider

(57) ABSTRACT

The present invention relates a method to make porous materials which are useful in pharmaceutical, medicine, industry, and agriculture. The most advantage of the porous materials is to provide extremely large surface area for further modification and to incorporate a bioactive reagent in a mild condition to make the porous materials bioactive, biocompatible and biodegradable.

11 Claims, 2 Drawing Sheets

Porous Material
taken under the microscopy at 40 time magnification

Porous Material
taken under the microscopy at 20 time magnification

Porous Material
taken under the microscopy at 20 time magnification

METHOD TO MAKE POROUS MATERIALS AND THEIR APPLICATIONS

FIELD OF THE INVENTION

The present invention relates to methods for making porous materials, which are useful in pharmaceutical, medicine, industry, and agriculture. The most advantage of the porous materials is to provide extremely large surface area for further modification and to incorporate a bioactive reagent in a mild condition to make the porous materials bioactive, biocompatible and biodegradable.

MAKING THE POROUS MATERIALS

Figure 1:
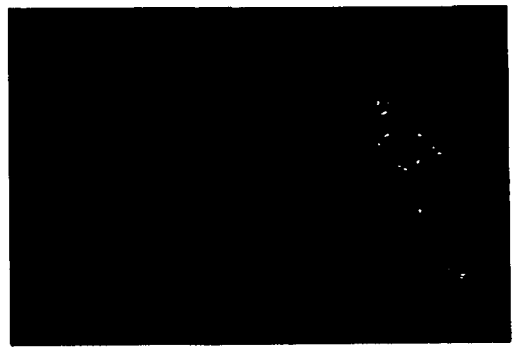
FIG. 1 shows a photograph of a porous material, which was taken under the microscopy at 40 times magnification.
Figure 2:
FIG. 2 shows a photograph of another porous material, which was taken under the microscopy at 20 times magnification.
Figure 3:
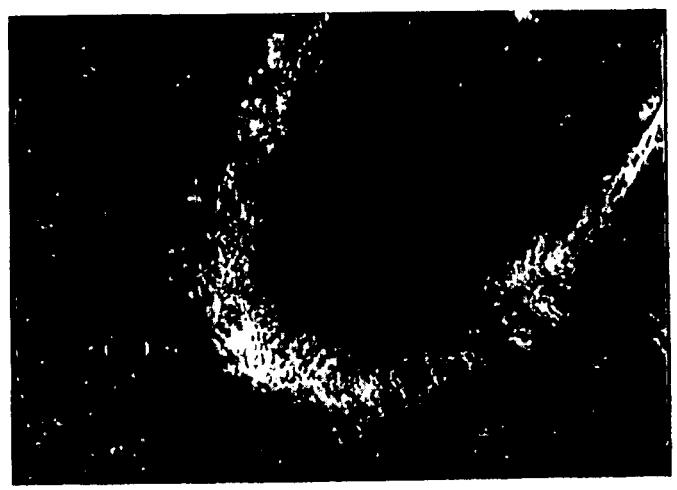
FIG. 3 shows a photograph of another porous material, which was taken under the microscopy at 20 times magnification.

Dissolving the material in solvent one, precipitating the material from the solution with solvent two, washing the precipitated material with water, and centrifuging the precipitated material; the porous material is made from freezing and thawing the precipitated material (Please see POROUS MATERIAL PHOTOGRAPHS).

Solvent one comprises of, but not limited to, an acid solvent, a base, an inorganic acid, an organic acid, an organic base, an organic base, a neutral solvent, and water.

Solvent two is used to precipitate the porous material from solution by neutralizing solution one or by changing the porous material's charge status in solution. Solvent two can comprise, but not limited to, a base, an inorganic base, an organic base, an acid, an inorganic acid, an organic acid, water. The selection of solution two depends on solution one. For example, if solution one is an acid, solution two may be a base.

The temperature of freezing the precipitated material is from −0.01 to −30° C., 30.1 to −80° C., −80.01° C. to −150° C., and −150.01° C. to −270° C.

The frozen material is modeled in, but not limited to, the shape of film, a sheet, a fiber, a column, a bead, a microsphere, a macrosphere, a square, a cube, coil, or other shapes.

The porous material provides much larger surface area than that of a solid material and may be further conjugated with the bioactive molecules. The conjugation of porous material with reactive molecules occurs with or without a linker.

The reactive molecules comprise of, but not limited to, an enzyme, an enzyme inhibitor, a tyrosine kinase inhibitor, a growth factor, vascular endothelial growth factor (VEGF), a growth factor inhibitor, a hormone, a hormone inhibitor, a ligand, a receptor, a receptor inhibitor, a peptide, a polylysine, a polyarginine, a nucleic acid, a nucleotide, a prodrug, a drug, an anticancer drug, an asparaginase, a monoclonal antibody, a cytokine, a chemokine, a chelator, a saccharide, a lipid, a pharmaceutical reagent, an electronic sensor, a photo sensor, a magnetic sensor, a pH sensor, a radiation enhancer, an immune modulator, a contrast reagent, an image reagent, a radionuclide, an ion channel inhibitor, a nanoparticle, a metal chelating complex, a labeling compound, a toxin, a boron, an arsenic trioxide, a radioactive halogen, an ion, or a derivative from molecules above.

Making the Reactive Porous Materials

Dissolving the material in the solvent one, precipitating the material from the solution with the solvent two, washing and centrifuging the precipitated material with solvent three (water or other solvents), adding reactive molecules such as the hormone(s) or other reactive molecules into the precipitated material, the reactive porous material is made from freezing and thawing the mixture of the precipitated material with the reactive molecules.

The reactive porous material is also made from conjugating the porous material with reactive molecules, such as a growth factor, a hormone, an antibody, a drug, an enzyme with linker or without linker.

The Reactive Molecules for Making Reactive Porous Materials

The reactive molecules to make reactive porous material comprise a polymer, a dendrimer, a nanomolecule, a chitosan, a chin, a protein, an enzyme, an enzyme inhibitor, a tyrosine kinase inhibitor, a growth factor, a growth factor inhibitor, a hormone, a hormone inhibitor, a ligand, a receptor, a receptor inhibitor, a peptide, a polylysine, a polyarginine, a nucleic acid, a nucleotide, a prodrug, a drug, anticancer drug, an asparaginase, a monoclonal antibody, a cytokine, a chemokine, a chelator, a saccharide, a lipid, a pharmaceutical reagent, an electronic sensor, a photo sensor, a magnetic sensor, a pH sensor, a radiation enhancer, an immune modulator, a contrast reagent, an image reagent, a radionuclide, a ion channel inhibitor, a nanoparticle, a metal chelating complex, a labeling compound, a boron, arsenic trioxide, a radioactive halogen, an ion, an acid, a base, or a derivative from the molecules above.

Protein

A protein is used for making a porous material, such as an albumin, collagen, a natural protein or a bioengineered protein.

Polymer

A polymer or a macromolecule with a hydrophilic group such as an amine, a carboxyl group is suitable for the invention.

Dendrimer

A dendrimer is a polymer in which the atoms are arranged in many branches and sub-branches along a central backbone of carbon atoms. It is a tree-like molecule with identical groups in the outer layer. It is built up from branched units called monomers.

A dendrimer and its derivative, for the purpose of the present invention, contain functional groups including, but not limited to, an amine, a carboxyl, a hydroxyl, or other hydrophilic group, which is able to conjugate with chelator molecules. The radionuclides and imaging agents bind to the chelator of the porous material.

Chitosan

In the present invention, chitosan is a natural polymer and has excellent biocompatibility. For instance, chitosan has been used in clinical trials for brachytherapy for liver cancer and rheumatoid arthritis. It has also been used in other clinical trials. Chitosan derivatives can also be used in the innovation.

Other polymers include, but not limited to, a polyacrylate, ethylene-vinyl acetate polymer, an acyl substituted cellulose acetate, a chin, a chitosan derivative(s), a polyurethane, a poly(vinyl imidazole), a chlorosulphonate polyolefin, polyethylene oxide, a polyphosphazine, a poly(vinyl alcohol), a polyamide, a polycarbonate, a polyalkylene, a polyacrylamide, a polyalkylene glycol, a polyalkylene oxide, a polyalkylene terephthalate, a polyvinyl ether, a polyvinyl ester, a polyvinylpyrrolidone, a polyglycolide, a polysiloxane, a alkyl cellulose, an hydroxyalkyl cellulose, a cellulose ether, a cellulose ester, and a nitrocellulose, a polyamino acid, a polyglutamic acid, a poly aspartic acid, a poly lysine, a polyarginine, a pectin, a hydroxypropylmethylcellulose, an ethylcellulose, an amylase, a dextran, a starch, a cyclodextrin, an inulin, and their derivatives or copolymers of the molecules above.

The mixture of claim 2, wherein the mixture comprises of, but not limited to, at least two of different molecules, such as the porous material ingredient and the reactive molecule. The ratio of reactive ingredient with porous material ingredient is at a proportion from 0.01-1:10, 1:11-20, 1:21-40, 1:41-60, 1:61-80, 1:81-99, or 1-10:1, 11-20:1, 21-40:1, 41-60:1, 61-80:1, 81-99:1.

Cross-Linking Reagent

The cross-linking reagent is selected from the group comprising of formaldehyde, glyceraldehyde, glutaraldehyde, dextran dialdehyde, ethylene glycol, di(ethylene glycol), polyethylene glycol, propylene glycol, di(propylene) glycol, polypropylene glycol, ethylene glycol dimethacrylate, di(ethylene glycol) dimethacrylate, poly(ethylene glycol) dimethacrylate, poly(lauryl methacrylate-co-ethylene glycol dimethacrylate), propylene glycol dimethacrylate, di(propylene glycol) dimethacrylate, poly(propylene glycol) dimethacrylate, malonic dihydrazide, ethylmalonic dihydrazide, succinic dihydrazide, glutaric dihydrazide, adipic dihydrazide, isophthalic dihydrazide, oxalyl dihydrazide, pimelic dihydrazide, 3,3'-sulfonyldibenzenesulfonic dihydrazide, m-xylylene isocyanate, 4-methyl-m-phenylene diisocyanate, 2-methyl-m-phenylene diisocyanate, 3,3'-dimethoxy-4,4'-biphenylene diisocyanate, 4-Br-6-methyl-1,3-phenylene diisocyanate, 4-Cl-6-methyl-1,3-phenylene diisocyanate, toluene 2,4-diisocyanate, 1,3-phenylene diisocyanate, 1,4-phenylene diisocyanate, 2,4,6-trimethyl-1,3-phenylene diisocyanate, 1,4-diisocyanatebutane, 1,6-diisocyanatehexane, 1,8-diisocyanateoctane, isophorone diisocyanate; carbodiimides such as N,N-(3-dimethylaminopropyl)-N-ethyl carbodiimide, calcium dichloride, divinylsulfone, sulfonylurea, hydrolysable polyrotaxane, L-lysine methyl ester, genipin and epicholordrin.

Conjugating the Chelator to the Porous Material

The Porous Material is further conjugated with chelators in order to bind radionuclides or a metal. Reaction conditions are shown by Example 5 and Example 6.

Chelator 1,4,7,10-tetraazacyclododecane-1,4,7,10-tetraacetic acid and cyclohexane-1,2-diamine-pentaacetic acid are chelators, which form extremely stable complexes with yttrium, indium, gadolinium and other metals after they conjugate to the porous material.

Other chelators include, but are not limited to, cyclohexyldiethylenetriaminepentaacetic acid ligand (CTPA), diethylenetriaminepentaacetic acid (DTPA), 1-(p-aminobenzyl)-DTPA, 1,6-diamino hexane-N,N,N',N'-tetraacetic acid, (DPDP), and ethylenebis(oxyethylenenitrilo)-tetraacetic acid (EGTA), ethylenediaminetetraacetic acid (EDTA), tetraazacyclotetradecane-N,N',N''N'''-tetraacetic acid (TETA), 6-[p-(bromoacetamido)benzyl]-TETA (BAT), N,N'-bis(hydroxybenzyl)-ethylenediamine-N,N'-diacetic acid (HBED), triethylene tetramine hexa-acetic acid (TTHA), hydroxyethyldiamine triacetic acid (HEDTA), hydroxyethylidene diphosphonate (HEDP), dimercaptosuccinic acid (DMSA), diethylenetriaminetetramethylenephosphonic acid (DTTP), 1,4,7,10 tetraazacyclododecane-1,4,7,10-tetra(methylene phosphonic acid) (DOTMP), methylbenzyldiethylene-triaminepentaacetic acid (MX-DTPA), bromoacetamidobenzyl-1,4,7,10-tetraazocyclododecane-N,N'N'',N'''-tetraacetic acid (BAD), 3,12-bis(carboxymethyl)-6,9-dioxa-3,12-diazatetradecanedioic acid, meso-2,3-dimercaptosuccinic acid (DMSA), the N(4),N(alpha),N(alpha),N(epsilon),N(epsilon)-pentakis[[((N-hydroxy-N-methyl]carbonyl)methyl]-2,6-diamino-4-azahexanoic hydrazide (5, DTPH), N-(2-hydroxyethyl)-ethylenediaminetriacetic acid (HEDTA), and trans-1,2-diaminocyclohexane-N,N,N',N'-tetraacetic acid (CDTA)

A Method of Labeling Radionuclide to the Chelator Conjugated Porous Material

The chelator-conjugated Porous Material binds the radionuclide forming the therapeutic reagent. The labeling procedure is shown by Example 7.

Radionuclide

The radionuclide in the present invention contains an alpha-emitter, beta-emitter, gamma-emitter, or the radionuclide, which can emit alpha-ray and beta-ray along with gamma-ray.

A radionuclide can be used within the scope of the invention. An element, with its isotope is selected from the groups comprising, but not limited to, yttrium, yttrium-90, indium, indium-111, technetium, technetium-99, holmium, holmium-166, lutetium, lutetium-177, rhenium, rhenium-186, rhenium-188), strontium, strontium-89, strontium-90, samarium, samarium-153, actinium, actinium-225, bismuth, bismuth-212, bismuth-213, lead, lead-212, radium, raium-223, radium-224, dysprosium, dysprosium-165, gold, gold-198, copper, copper-67, scandium, scandium-47, gallium, gallium-67, rhodium, rhodium-10,5 praseodymium, praseodymium-142, neodymium, neodymium-147, promethium, promethium-151, gadolinium, gadolinium-159, thorium, thorium-167, europium, europium-152, erbium, erbium-169, erbium-171, thallium, thallium-201, palladium, palladium-103, astatine, astatine-211, iodine, iodine-123, iodine-125, iodine-131, phosphorus, phosphorus-32.

A New Therapeutic Reagent Made of the Porous Material

The radionuclide bound porous material is a new therapeutic reagent. It makes delivery of a killing dose of radiation to all solid tumors achievable.

The radionuclide bonded porous material is administered by local injection into the tumor site, which significantly increases the radiation dose to the tumor. The therapeutic reagent can also be administered systemically especially when the radionuclide bonded porous material is linked to an antibody, a hormone, a receptor, and/or ligands.

The radionuclide bonded porous material can further comprise of, but not limited to, a small amount of an imaging reagent, such as gadolinium, iron, manganese, which is bound to the conjugated chelator in the porous material.

Application

The porous material is useful in making a therapeutic reagent in the treatment of a primary and a secondary tumor, a hyperplasia disorder in breast, uterus, prostate and heart or other diseases.

The reactive porous material can also be combined with chemotherapy, monoclonal antibody therapy, tumor vaccination or cellular immunotherapy for the treatment of a tumor.

The porous material is a carrier for drug delivery.

The porous material is a metal ion capturer for a metal recycling, and the purification of water and a solution.

The porous material is useful in implementing a pH sensitive controlled release of a drug, or a reactive reagent.

The porous material is useful in controlling the release of a drug or other material.

The porous material is useful in detecting a photon, and in capturing a photon.

The porous material is useful in electron detection, conduction and capture.

The porous material is useful in signal detection, transduction, transformation, and signal storage.

The porous material is useful in energy transformation, such as transforming electromagnetic waves into heat.

The porous material is useful in labeling an item, such as for tracing an item in the supply chain.

The porous material is useful in nitrogen capturing and in the controlled release of a fertilizer, an insecticide, and/or a hormone.

EXAMPLES

Example 1

Method to Make the Porous Material

Ten milliliter of 10% albumin or/and collagen or/and elastin solution was denatured with 1.0 Normal 10 mL of hydrogen chloride (solvent one) for 2 hours, centrifuged at 1500 rpm, washed with water for at least three times until the pH in the washing liquid reached 7.0, or precipitating the protein by ultracentrifugation, frozen at −80° C. overnight, modeled in a shape of a bead, a sheet, a film, a column etc. The porous bead, porous film and porous column may have been further conjugated with other molecule such as a chelator or a drug with or without a linker.

Example 2

Method to Make the Porous Material

One gram chitosan was dissolved in 50 mL of 2% acetic acid (solvent one), precipitated with 1.0 Normal of sodium hydroxide (solvent two) and centrifuged, washed with water for at least three times until the pH in the washing liquid reached 7.0, frozen at −80° C. overnight, modeled in a shape of a bead, a sheet, a film a column etc. The porous bead, porous film and porous column may have been further conjugated with other molecule such as chelator or a drug with or without a linker.

Example 3

Crosslinking the Albumin Porous Material

Epicholordrin (0.49 ml) was added to a suspension of 1.0 g albumin porous material in 10 ml of water and maintained at 50° C. for 1 h. Subsequently 7 ml of 0.1 N NaOH was added and was boiled for 2 h. The porous particle was sequentially rinsed with water, 0.1 M hydrochloric acid, and 0.1 N NaOH, and finally washed with water.

Example 4

Crosslinking the Chitosan Porous Material

The chitosan porous material was immersed in an aqueous solution of glutaraldehyde (2.5% w/v) for 24 h, and then washed with water for three times.

Example 5

Conjugation of the DOTA on the Albumin Porous Material

The albumin porous material was immersed in HEPES 0.1 M (pH8.5). A 10 mg/ml solution of chelator (DOTA) in ethanol was added dropwise to the particle HEPES solution. The ratio of DOTA to porous material (mg/mg) is approximately 1:10-1:20, 1:21-1:40, 1:41-1:60, 1:61-1:80, 1:81-1:100. The reaction was allowed to proceed and stirred overnight at 37.0° C. The material was washed with water three times to remove the unbound chelator.

Example 6

Conjugation of the DTPA on the Chitosan Porous Material

The chitosan porous material was immersed in HEPES 0.1 M (pH8.5). A 10 mg/ml solution of chelator (DTPA) in ethanol was added dropwise to the material HEPES solution. The ratio of DTPA to material (mg/mg) is approximate 1:10-1:20, 1:21-1:40, 1:41-1:60, 1:61-1:80, 1:81-1:100. The reaction was allowed to proceed and stirred overnight at 37.0° C. The material was washed with water three times to remove the unbound chelator.

Example 7

Radiolabeling with Indium

One milligram of the albumin porous material was immersed in 0.1 M ammonium acetate buffer for 30 minutes. Two mCi of indium was added into the chelator-porous material buffer solution and incubated for 30 minutes at 37° C.

Example 8

Radiolabeling with Yttrium-90

One milligram of the dendrimer porous material was immersed in 0.1 M ammonium acetate buffer. Two mCi of yttrium was added into the chelator-porous material solution and incubated for 30 minutes at 37° C.

Example 9

Murine Melanoma Tumor Model in C57 Black Mice

A mouse with a tumor size of about 0.125 cm3 size was randomly assigned to either a control group or a treated group. There were three groups: PBS control, Y-90-DTPA treated group, and Y-90-albumin-porous material treated group. Each group included fifteen mice. Each tumor size had been measured every three days since treatments started. When the tumor volume reached 2 cm3, the tumor bearing mouse was euthanized. A 500 μCi of Y-90-albumin porous material was given locally once. A 500 μCi of Y-90-DTPA or PBS (equal volume to the Y-90-albumin porous particle) was given locally once in other group.

Tumor Volume and Survived Mice

| Groups | Mean of Tumor Volume on Day 15 after Treatment Started | Mice survived after Treatment Started |
|---|---|---|
| PBS control | 1.86 ± 0.31 cm$^3$ | All died by day 24 |
| Y-90-DTPA | 1.74 ± 0.31 cm$^3$ | All died by day 25 |
| Y-90-albumin porous material | undetectable | 14/15 mice survived on day 100 |

Example 10

Breast Cancer Model (BT-474) in Nude Mice

A mouse with a tumor size of about 0.125 cm3 size was randomly assigned to either a control group or a treated group. There were four groups: PBS control, unmodified antibody (Trastuzumab), Y-90-Trastuzumab and Y-90-dendrimer porous material treated group. Each group was fifteen mice. Each tumor size had been measured every three days since treatments started. When the tumor volume reached 2 cm3, the tumor bearing mouse was euthanized. Unmodified Trastuzumab was given i.v. at the dose of 1 mg/kg every weekly for whole experiment period. A 100 µCi of Y-90 labeled Trastuzumab was given i.v. at once (maximal tolerant dose) and a 600 µCi of Y-90-dendrimer porous material was given locally once.

Tumor Volume

| Groups | Tumor Volume cm$^3$ Day 40 after Treatment Started | Day Mice survived after Treatment Started |
|---|---|---|
| PBS control | 1.86 ± 0.58 | All mice euthanized by day 45 |
| Unmodified Trastuzumab | 1.75 ± 0.49 | All mice euthanized by day 47 |
| Y-90-Trastuzumab | 1.70 ± 0.41 | All mice euthanized by day 50 |
| Y-90-dendrimer porous material | 0.00 | All mice survived on day 150 |

Example 11

Colorectal Cancer Model (HT-29) in Nude Mice

A mouse with a tumor size of about 0.125 cm3 size was randomly assigned to either a control group or a treated group. There were four groups: PBS control, unmodified antibody (cetuximab), Y-90-cetuximab and Y-90-chitosa porous material treated group. Each group was fifteen mice. Each tumor size had been measured every three days since treatments started. When the tumor volume reached 2 cm3, the tumor bearing mouse was euthanized. Unmodified cetuximab was given i.v. at the dose of 1 mg/kg every weekly for whole experiment period. 100 µCi of Y-90 labeled cetuximab was given i.v. once (maximal tolerated dose of radiolabeled antibody) and 600 µCi of Y-90-chitosan porous material was given locally once.

Tumor Volume

| Groups | Tumor Volume cm$^3$ Day 50 after Treatment Started | Day Mice survived after Treatment Started |
|---|---|---|
| PBS control | 1.86 ± 0.58 | All mice euthanized by day 65 |
| Unmodified Cetuximab | 1.75 ± 0.49 | All mice euthanized by day 69 |
| Y-90- Cetuximab | 1.70 ± 0.41 | All mice euthanized by day 73 |
| Y-90-chitosan porous material | undetectable | All mice survived on day 180 |

Example 12

Chondrocytes are harvested from Non-weight-bearing joint surface or other cartilage tissues and cultured in the porous material to a cartilage tissue sheet to repair the damaged surface.

Example 13

Skin cells, fibroblasts or stem cells are cultured in the porous material and then implanted for burn therapy or other diseases.

Example 14

Engineered insulin expression cells, stem cells or pancreas islet cells are cultured in porous materials and implanted into a patient for treating diabetes.

Example 15

VEGF is added into precipitated collagen and frozen into a porous material which formulates a slow release VEGF product and then the slow release VEGF product is implanted into ischemic area for heart diseases or implanted for other diseases.

REFERENCES

1. Hepatocellular carcinoma: pilot trial of treatment with Y-90 microspheres. By Houle S, Yip T K, Shepherd F A, Rotstein L E, Sniderman K W, Theis E, Cawthorn R H, Richmond-Cox K. Radiology. 1989 September; 172(3):857-60.
2. A phase I dose escalation trial of yttrium-90 microspheres in the treatment of primary hepatocellular carcinoma. By Shepherd F A, Rotstein L E, Houle S, Yip T C, Paul K, Sniderman K W. Cancer. 1992 Nov. 1; 70(9):2250-4.
3. Hepatocellular carcinoma: pilot trial of treatment with Y-90 microspheres. By Houle S, Yip T K, Shepherd F A, Rotstein L E, Sniderman K W, Theis E, Cawthorn R H, Richmond-Cox K. Radiology. 1989 September; 172(3):857-60.

The invention claimed is:

1. A method of making a porous material comprising: dissolving a material in a solvent one, precipitating the material with a solvent two, washing and centrifuging the precipitated material with a solvent three, modeling the precipitated material in the shape of a macrosphere, a bead, a column, a film, a square, a cube, a coil, or a sheet, freezing the precipitated material at about −80° C. to form the porous material, and thawing the porous material, wherein the porous material is useful in pharmaceutical, medicine, industry, and agriculture applications and wherein the material is selected from the group consisting of an albumin or a chitosan.

2. The method of claim 1 further comprising conjugating the porous material with a substrate.

3. The method of claim 2, wherein the substrate is selected from the group consisting of a chelator, a drug, a prodrug, a peptide, a protein, an enzyme, an enzyme inhibitor, a cytokine, a chemokine, a hormone, hormone inhibitor, a growth factor, a growth factor inhibitor, a receptor, a receptor inhibitor, a ligand, a lipid, a nucleotide, a electronic sensor, a photo sensor, a magnetic sensor, a pH sensor, a reactive molecule, and a pharmaceutical reagent.

4. The method of claim 3, wherein the substrate is conjugated to the porous material with or without a linker.

5. The method of claim 4, wherein the linker is selected from the group consisting of formaldehyde, glyceraldehyde, glutaraldehyde, dextran dialdehyde, and ethylene glycol.

6. The method of claim 2 further comprising binding the substrate to a radionuclide or a metal ion to form a therapeutic reagent.

7. The method of claim 6, wherein the radionuclide is selected from the groups consisting of an alpha-emitting radionuclide, a beta-emitting radionuclide and a gamma-emitting radionuclide.

8. The method of claim 6, wherein the radionuclide is selected from the group consisting of yttrium-90, holmium (166Ho), lutetium (177Lu), rhenium, (Re-186, Re-188), strontium (89Sr, 90Sr), samarium (153Sm), actinium (225Ac), bismuth (212Bi, 213Bi), lead (212Pb), radium, dysprosium (165Dy), gold (198 Au), copper (67Cu), scandium (47Sc), gallium (67Ga), rhodium (105Rh), praseodymium (142Pr), neodymium (147Nd), promethium (151Pm), gadolinium (159Gd), thorium (161Th), europium (152Eu), erbium (169Er, 171Er), thallium (201Tl), palladium (Pd103), astatine (211At), iodine (123I, 125I, and 131I), and phosphorus (32 P).

9. The method of claim 1, wherein the solvent one is selected from the soup consisting of an organic acid, an inorganic acid, an organic base, an inorganic base, and water.

10. The method of claim 1, wherein the solvent two from the group consisting of an organic base, an inorganic base, an organic acid, an inorganic acid, and water, and selection of solvent two is depend on what type of solvent one is used.

11. The method of claim 1, wherein the solvent three is water.

* * * * *